US00PP28452P2

(12) United States Plant Patent
Trees

(10) Patent No.: US PP28,452 P2
(45) Date of Patent: Sep. 26, 2017

(54) ***VERBENA* PLANT NAMED 'BALENDMAG'**

(50) Latin Name: *Verbena×hybrida*
Varietal Denomination: Balendmag

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 6 days.

(21) Appl. No.: 14/999,299

(22) Filed: Apr. 21, 2016

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Keith Robinson
(74) *Attorney, Agent, or Firm* — Audrey Charles

(57) ABSTRACT

A new and distinct cultivar of *Verbena* plant named 'Balendmag', characterized by its dark red-purple colored flowers, dark green-colored foliage, and vigorous, spreading-trailing growth habit, is disclosed.

1 Drawing Sheet

GOVERNMENT RIGHTS NOTICE

The Government has rights in this invention pursuant to Strategic Partnership Projects (SPP) Agreement FRA-2015-0011.

Latin name of genus and species of plant claimed: *Verbena×hybrida.*

Variety denomination: 'Balendmag'.

BACKGROUND OF THE INVENTION

The present invention relates to a new and distinct cultivar of *Verbena* plant botanically known as *Verbena×hybrida* and hereinafter referred to by the cultivar name 'Balendmag'.

The new cultivar originated in a controlled breeding program in Arroyo Grande, Calif. The objective of the breeding program was the development of *Verbena* cultivars that are durable to environmental stresses, have dark green-colored foliage, and a spreading-trailing growth habit.

The new *Verbena* cultivar is an irradiation-induced sport of EnduraScape Purple Improved 'Balendurim', co-pending application U.S. Plant patent application Ser. No. 14/999,300, characterized by its dark purple-colored flowers, dark green-colored foliage, and vigorous, spreading-trailing growth habit. The irradiation occurred in February 2010. The new cultivar was discovered as a side shoot and selected during July 2010 in a controlled environment in Arroyo Grande, Calif.

Asexual reproduction of the new cultivar by terminal stem cuttings since July 2010 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balendmag' as a new and distinct cultivar of *Verbena* plant:

1. Dark red-purple colored flowers;
2. Dark green-colored foliage; and
3. Vigorous, spreading-trailing growth habit.

Plants of the new cultivar differ from plants of the parent primarily in flower color.

Of the many commercially available *Verbena* cultivars, the most similar in comparison to the new cultivar is EnduraScape Lavender 'Balendav', U.S. Plant patent application Ser. No. 13/999,724, now abandoned. However, in side by side comparisons, plants of the new cultivar differ from plants of 'Balendav' in at least the following characteristics:

1. Plants of the new cultivar have a flower color different from plants of 'Balendav'; and
2. Plants of the new cultivar are wider than plants of 'Balendav'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balendmag'. The plants were grown in 4.5-inch pots for 9 weeks in a greenhouse in West Chicago, Ill. Plants were given one pinch at transplant.

DETAILED BOTANICAL DESCRIPTION

Figure 1:
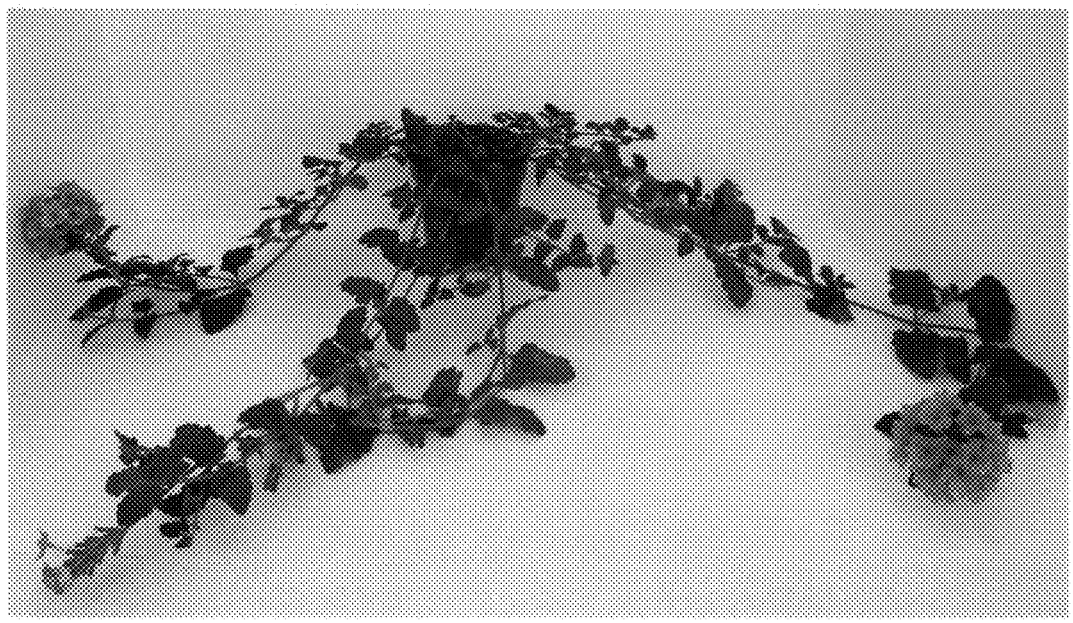
FIG. 1 illustrates a side view of the overall growth and flowering habit of 'Balendmag'.
Figure 2:
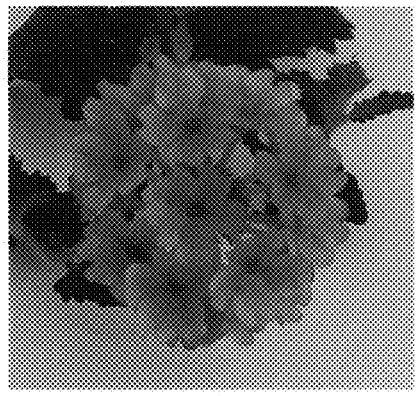
FIG. 2 illustrates a close-up view of an individual inflorescence of 'Balendmag'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in April 2016 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 9 weeks utilizing a soilless growth medium. Plants were given one pinch at transplant. Greenhouse temperatures were maintained at approximately 66° F. to 70° F. (19° C. to 21° C.) during the day and approximately 58° F. to 62° F. (14° C. to 17° C.) during the night. Greenhouse light levels of 2,500 footcandles to 6,000 footcandles were maintained during the day. Measurements and numerical values represent averages of typical plants.

Botanical classification: *Verbena×hybrida* cultivar 'Balendmag'.

Parentage:

*Parent*.—EnduraScape Purple Improved 'Balendurim', co-pending application U.S. Plant patent application Ser. No. 14/999,300.

Propagation:

*Type cutting*.—Terminal stem.

*Time to initiate roots*.—Approximately 6 to 9 days.

*Time to produce a rooted cutting*.—Approximately 24 to 28 days.

*Root description*.—Fibrous.

*Rooting habit*.—Freely branching.

Plant description:

*Commercial crop time*.—Approximately 5 to 7 weeks from a rooted cutting to finish in a 10 cm pot.

*Growth habit and general appearance*.—Vigorous, spreading-trailing.

*Size*.—Height from soil level to top of plant plane: Approximately 4.0 cm. Width: Approximately 89.0 cm.

*Branching habit*.—Freely branching, pinching enhances basal branching. Quantity of main branches per plant: Approximately 3.

*Branch*.—Shape: Square in cross section. Strength: Strong. Length: Approximately 43.0 cm. Diameter: Approximately 3.0 mm. Length of central internode: Approximately 6.0 cm. Texture: Densely pubescent with a mixture of glandular and nonglandular hairs. Gland color: Mixture of N92A and colorless, transparent. Color of young stems: 144A. Color of mature stems: 138A.

Foliage description:

*General description*.—Quantity of leaves per main branch: Approximately 16. Fragrance: None. Form: Simple. Arrangement: Opposite.

*Leaves*.—Aspect: Perpendicular to stem, obtuse angle with age. Shape: Ovate. Margin: Serrate Apex: Broadly acute to rounded. Base: Truncate. Venation pattern: Pinnate. Length of mature leaf: Approximately 4.5 cm. Width of mature leaf: Approximately 3.3 cm. Texture of upper surface: Moderately pubescent. Texture of lower surface: Densely pubescent with a mixture of glandular and nonglandular hairs. Gland color: Colorless, transparent. Color of upper surface of young and mature foliage: Closest to but darker than N137A with venation of 147C. Color of lower surface of young and mature foliage: Closest to 138A with venation of 147C.

*Petiole*.—Length: Approximately 9.0 mm. Diameter: Approximately 2.0 mm. Texture: Densely pubescent with a mixture of glandular and nonglandular hairs. Gland color: Mixture of N92A and colorless, transparent. Color: 147C to 147D.

Flowering description:

*Flowering habit*.—'Balendmag' is freely flowering under outdoor growing conditions with substantially continuous blooming from spring through autumn and year-round in greenhouse environment.

*Lastingness of individual flower on the plant*.—Approximately 5 to 7 days.

Inflorescence description:

*General description*.—Type: Corymb. Shape: Hemispherical. Quantity per plant: Approximately 2. Fragrance: None. Length or height: Approximately 4.0 cm. Width: Approximately 5.7 cm. Quantity of fully open flowers per inflorescence: Approximately 20.

*Peduncle*.—Strength: Strong. Aspect: Erect. Length: Approximately 5.5 cm. Diameter: Approximately 2.0 mm. Texture: Densely pubescent with a mixture of glandular and nonglandular hairs. Gland color: Mixture of N92A and colorless, transparent. Color: 138A.

Flower description:

*General description*.—Type: Sessile, salverform.

*Bud*.—Rate of opening: Generally takes 2 to 3 days for bud to progress from first color to fully open flower. Quantity of unopened inflorescences per plant: Approximately 2.

*Bud just before opening*.—Shape: Elongated, globular at apex. Length: Approximately 1.2 cm. Diameter: Approximately 2.0 mm. Color: Petal portion N78D, sepal portion 137B.

*Corolla*.—Shape: Round. Diameter: Approximately 2.0 cm. Depth: Approximately 3.2 cm.

*Petals*.—Quantity: 5, fused at base forming a tube. Shape: Obovate. Appearance: Dull. Margin: Entire. Apex: Emarginate. Length of upper petals from tube: Approximately 9.0 mm. Width of upper petals: Approximately 7.0 mm. Length of lateral petals from tube: Approximately 9.0 mm. Width of lateral petals: Approximately 8.0 mm. Length of lower petal from tube: Approximately 1.0 cm. Width of lower petal: Approximately 1.0 cm. Texture of upper surface: Upper petals glabrous, base of lateral on lower petals glandular pubescent. Texture of lower surface: Sparsely pubescent with a mixture of glandular and nonglandular hairs. Gland color: Mixture of N92A and colorless, transparent. Color of upper surface when first open: Closest to N66A with a central overlay of N88A. Color of lower surface when first open: Closest to N66B with a central overlay of N88D. Color of upper surface when fully open: Closest to N74B with a central overlay of N88A. Color of lower surface when fully open: 75A with a faint central overlay of N88D. Color of whiskers surrounding the opening of the corolla tube: N88D.

*Corolla tube*.—Length: Approximately 2.5 cm. Diameter at proximal end: Approximately 1.0 mm. Diameter at distal end: Approximately 2.0 mm. Texture of inner and outer surfaces: Upper half densely pubescent, lower half glabrous. Color of inner and outer surfaces: 145D.

*Calyx*.—Shape: Tubular with 5 acute tips. Length: Approximately 1.2 cm. Width: Approximately 2.0 mm.

*Sepals*.—Quantity per flower: 5, fused at base. Shape: Linear. Apex: Acute. Length: Approximately 1.2 cm. Width: Approximately 1.0 mm. Texture of inner surface: Moderately pubescent. Texture of outer surface: Densely pubescent with a mixture of glandular and nonglandular hairs. Gland color: Mixture of N92A and colorless, transparent. Color of inner and outer surfaces: 137B.

*Stipules*.—Shape: Lanceolate. Apex: Acute. Length: Approximately 6.0 mm. Width at base: Approximately 2.0 mm. Texture of inner surface: Densely pubescent. Texture of outer surface: Densely pubescent with a mixture of glandular and nonglandular hairs. Gland color: Mixture of N92A and colorless, transparent. Color of inner and outer surfaces: 144A at base transitioning to 137A at apex.

*Reproductive organs*.—Androecium: Stamen quantity: 4, didynamous. Stamen length of longer pair: Approximately 2.0 mm. Stamen length of shorter pair: Approximately 1.0 mm. Anther shape: Bilobed, ovoid. Anther length: Approximately 1.0 mm. Anther color: 154C. Pollen amount: Moderate. Pollen color: 11D. Gynoecium: Pistil quantity: 1 per flower. Pistil length: Approximately 2.1 cm. Stigma shape: Bifid. Stigma length: Less than 1.0 mm. Stigma color: 139B. Style length: Approximately 2.0 cm. Style color: 145D tinted with 187A near stigma. Ovary diameter: Approximately 1.0 mm. Ovary texture: Glabrous. Ovary color: N144C.

Seed and fruit production: Neither seed nor fruit production has been observed.

Disease and pest resistance: Resistance to pathogens and pests common to *Verbena* has not been observed.

What is claimed is:

1. A new and distinct cultivar of *Verbena* plant named 'Balendmag', substantially as herein illustrated and described.

* * * * *